US008453268B2

(12) United States Patent
Ahlgren et al.

(10) Patent No.: US 8,453,268 B2
(45) Date of Patent: Jun. 4, 2013

(54) HEAD SUSPENSION HEADBAND

(75) Inventors: Lars-Olov Ahlgren, Fellingsbro (SE); Oskar E. Juhlin, Gustavsberg (SE)

(73) Assignee: 3M Innovative Properties Company, St. Paul, MN (US)

( * ) Notice: Subject to any disclaimer, the term of this patent is extended or adjusted under 35 U.S.C. 154(b) by 347 days.

(21) Appl. No.: 12/681,847

(22) PCT Filed: Oct. 6, 2008

(86) PCT No.: PCT/US2008/078896
§ 371 (c)(1),
(2), (4) Date: Apr. 6, 2010

(87) PCT Pub. No.: WO2009/048829
PCT Pub. Date: Apr. 16, 2009

(65) Prior Publication Data
US 2010/0235971 A1 Sep. 23, 2010

Related U.S. Application Data

(60) Provisional application No. 60/978,819, filed on Oct. 10, 2007.

(51) Int. Cl.
*A42B 3/00* (2006.01)
(52) U.S. Cl.
USPC ............................................. 2/416
(58) Field of Classification Search
USPC ............. 2/410, 411, 416, 417, 418, 419, 421, 2/422, 209.3, 209.4, 8.1, 8.2, 424; 602/17, 602/74; 128/870, 97.1, 857, 863, 207.11, 128/207.17, 206.21, 206.24
See application file for complete search history.

(56) References Cited

U.S. PATENT DOCUMENTS

| | | | | |
|---|---|---|---|---|
| 1,140,812 A | * | 5/1915 | Getler | 2/182.4 |
| 1,170,052 A | * | 2/1916 | Diener et al. | 2/181.6 |
| 1,207,137 A | * | 12/1916 | Clore | 2/181.8 |
| 2,160,567 A | | 9/1937 | Sterne | |
| 3,500,474 A | | 3/1970 | Austin | |
| 3,906,548 A | | 9/1975 | Kallis | |
| 4,888,831 A | | 12/1989 | Oleson | |
| 4,942,628 A | | 7/1990 | Freund | |
| 5,077,836 A | | 1/1992 | Idoff | |
| 5,571,217 A | | 11/1996 | Del Bon et al. | |
| 5,572,746 A | * | 11/1996 | Linico | 2/182.1 |
| 5,608,917 A | | 3/1997 | Landis | |
| 5,787,507 A | * | 8/1998 | Sullivan | 2/182.1 |
| 5,896,586 A | | 4/1999 | Freund | |
| 6,341,382 B1 | | 1/2002 | Ryvin | |
| 6,367,085 B1 | * | 4/2002 | Berg | 2/202 |
| 6,691,322 B2 | * | 2/2004 | Held | 2/184.5 |
| 6,966,074 B2 | * | 11/2005 | Huh | 2/414 |
| 7,213,271 B1 | | 5/2007 | Bielefeld | |
| 2007/0245466 A1 | * | 10/2007 | Lilenthal et al. | 2/416 |

FOREIGN PATENT DOCUMENTS

| | | |
|---|---|---|
| AU | 39234/68 | 12/1970 |
| CN | 2 724 450 | 9/2005 |
| RU | 2223683 | 2/2004 |
| RU | 2238507 C1 | 10/2004 |

\* cited by examiner

*Primary Examiner* — Khoa Huynh
*Assistant Examiner* — Anna Kinsaul
(74) *Attorney, Agent, or Firm* — Kenneth B. Wood

(57) ABSTRACT

A head suspension headband includes an elongated headband having a band length and configured to be disposed across a forehead of a user, and a plurality of suspension elements disposed along the band length and configured to contact the forehead of a user.

19 Claims, 4 Drawing Sheets

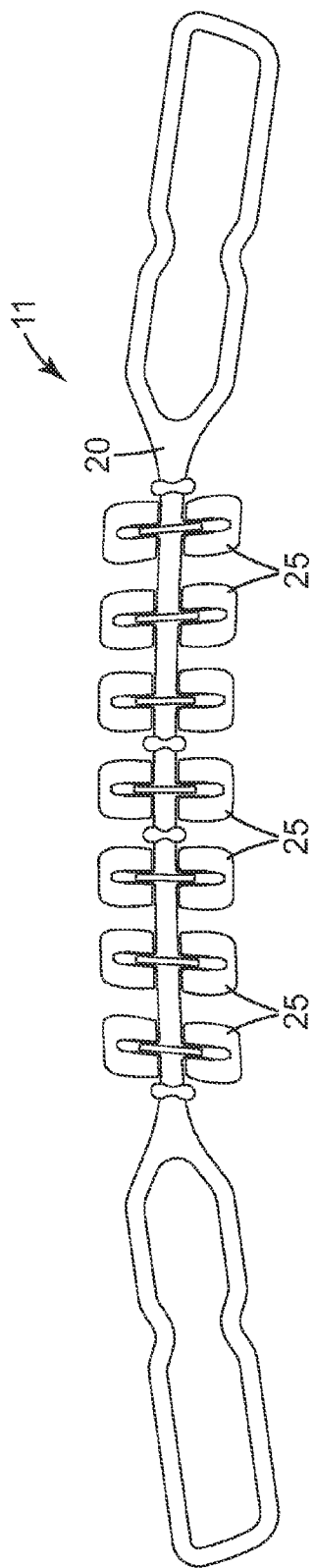
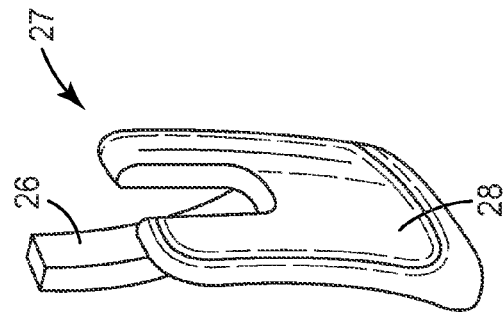
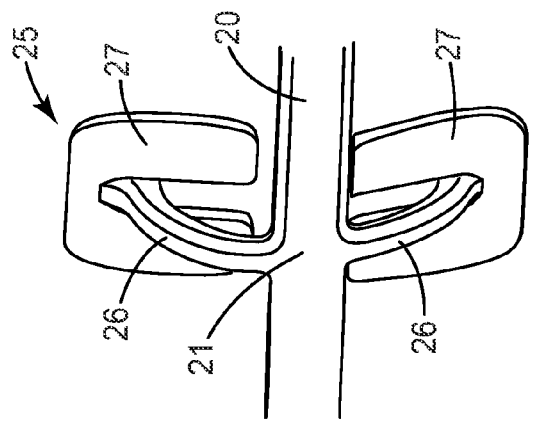

HEAD SUSPENSION HEADBAND

CROSS REFERENCE TO RELATED APPLICATIONS

This application is a national stage filing under 35 U.S.C. 371 of PCT/US2008/078896, filed Oct. 6, 2008, which claims priority to U.S. Provisional Application No. 60/978,819, filed Oct. 10, 2007, the disclosure of which is incorporated by reference in its/their entirety herein.

FIELD

The present disclosure relates to a head suspension headband and particularly to a head suspension headband having a plurality of suspension members disposed along a length thereof.

BACKGROUND

Protective headgear, for example construction hard hats, helmets, such as fire fighter helmets, shields such as welding shields and grinding shields, sports equipment headgear, and the like often include a headgear support or head suspension. The headgear supports or head suspension often include with headbands and/or head straps that are adjustable so that the headgear can be supported comfortably on any size head by the headband.

In many headgear supports or head suspensions, it is desired that the headband be easy to adjust and that it fit adequately without discomfort to the user. In some cases, it is also desired that headgear supports or head suspension headbands do not require that the headgear be removed from the user's head in order to make adjustments in the size of the head suspension. Furthermore, it is desired that the head suspension be comfortable to wear for extended periods of time without excessive need of re-positioning or adjustments. Accordingly, there is a need for head suspensions that are more comfortable to wear for longer periods of time and that are easier to adjust.

BRIEF SUMMARY

The present disclosure relates to a head suspension headband and particularly to a head suspension headband having a plurality of suspension members disposed along a length thereof.

In a first embodiment, a head suspension headband includes an elongated headband having a band length and configured to be disposed across a forehead of a user, and a plurality of suspension elements disposed along the band length and configured to contact the forehead of a user.

In another embodiment, a head suspension headband includes an elongated headband having a band length and configured to be disposed across a forehead of a user, and a plurality of suspension elements disposed along the band length and configured to contact the forehead of a user. Each suspension element includes a pair of strut elements that extend away from each other and away from the elongated headband and a forehead contact pad attached to each strut element.

In a further embodiment, a head protection device includes a head suspension headband having an elongated headband with a band length and configured to be disposed across a forehead of a user, and a head protection element attached to the head suspension headband. A plurality of suspension elements are disposed along the band length and configured to contact the forehead of a user.

BRIEF DESCRIPTION OF THE DRAWINGS

The invention may be more completely understood in consideration of the following detailed description of various embodiments of the invention in connection with the accompanying drawings, in which:

FIG. 4 is a schematic front plan view of an illustrative head band front portion;

FIG. 5 is a schematic perspective view of an illustrative suspension element;

FIG. 6 is a schematic perspective view of an illustrative contact pad; and

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

In the following description, reference is made to the accompanying drawings that form a part hereof, and in which are shown by way of illustration several specific embodiments. It is to be understood that other embodiments are contemplated and may be made without departing from the scope or spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

The present disclosure relates to a head suspension headband and particularly to a head suspension headband having a plurality of suspension members disposed along a length thereof. Suspension members or elements may serve to lift and, preferably, to suspend at least a portion of the headband over the forehead of a user. These disclosed headbands are designed with the goal of being more comfortable to wear for extended periods of time and reduce the need for the user to re-position or adjust the headgear supports or head suspension headband during use. The disclosed head suspension headband design aims to increase user comfort by increasing the contact surfaces between the suspension elements and the user forehead and reducing contact with some of the most sensitive area of the skull. In addition, the disclosed head suspension headband design aims to increase user comfort by allowing the suspension elements to self-adjust to the user's forehead. While the present invention is not so limited, an appreciation of various aspects of the invention will be gained through a discussion of the examples provided below.

Figure 1:
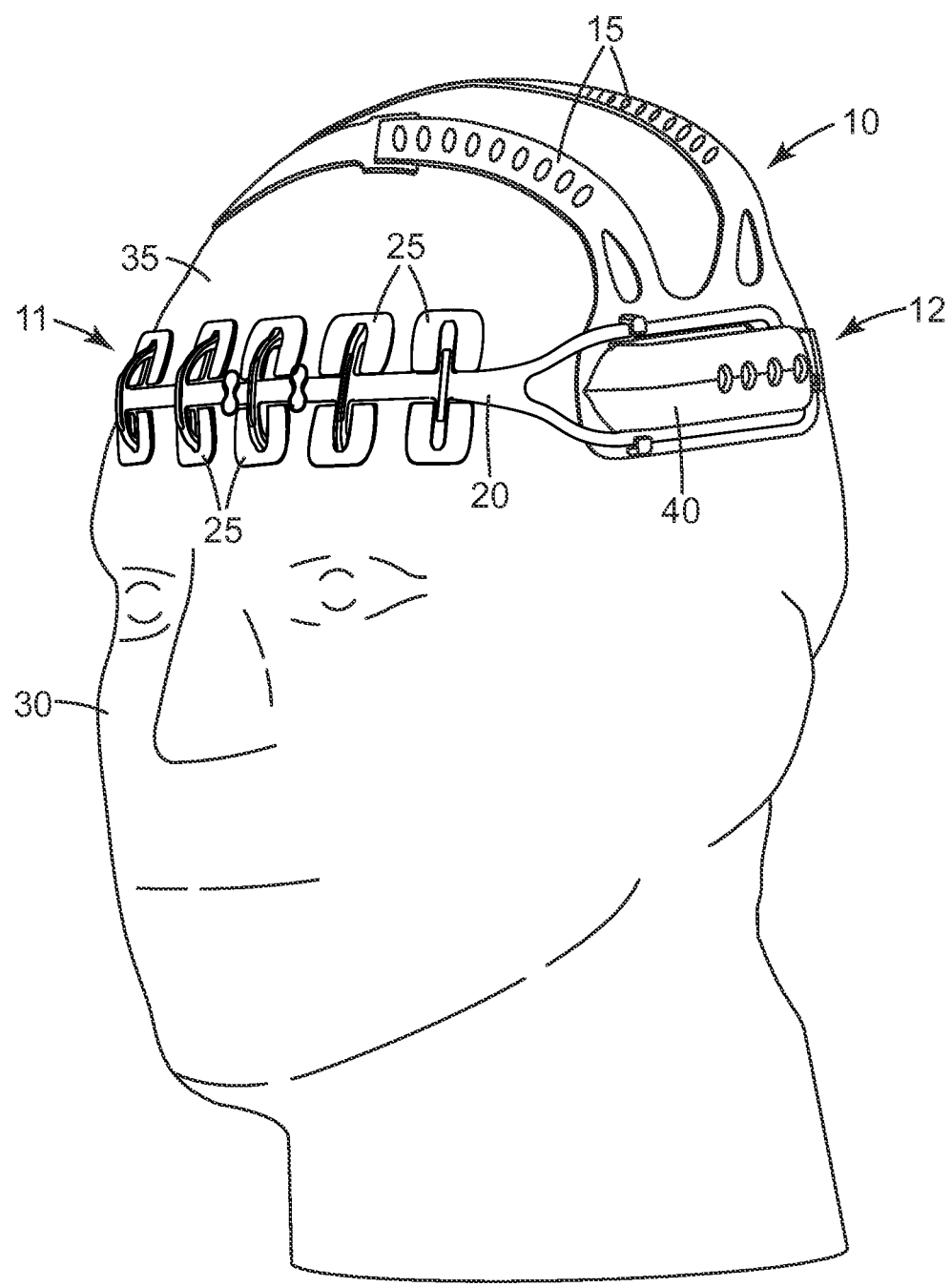
FIG. 1 is a schematic front perspective view of an illustrative head suspension.
Figure 2:
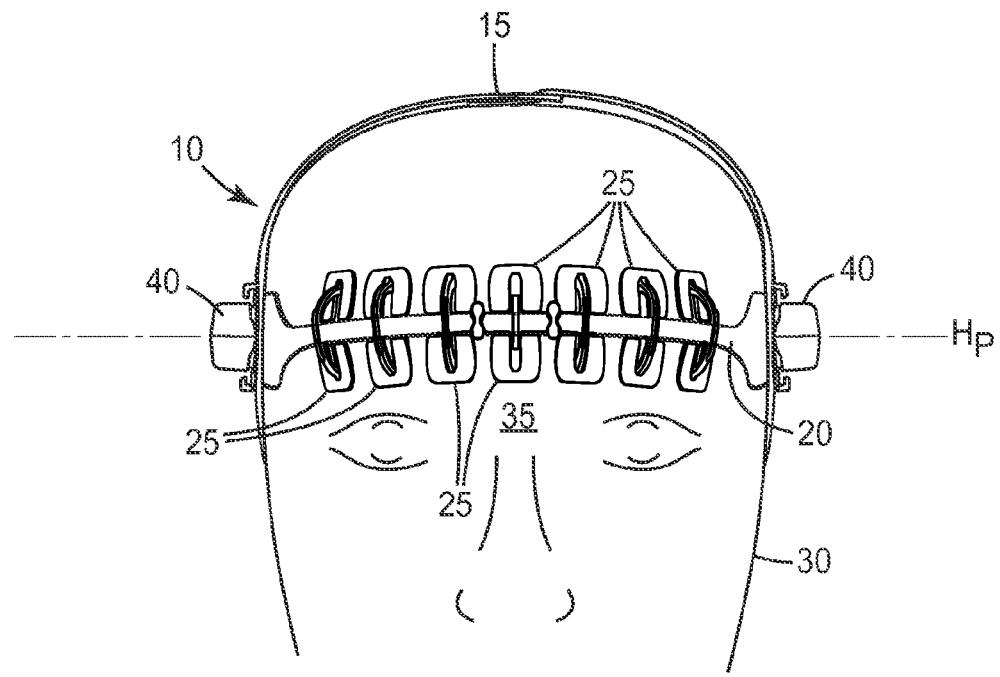
FIG. 2 is a schematic front elevation view of the illustrative head suspension shown in FIG. 1.
Figure 3:
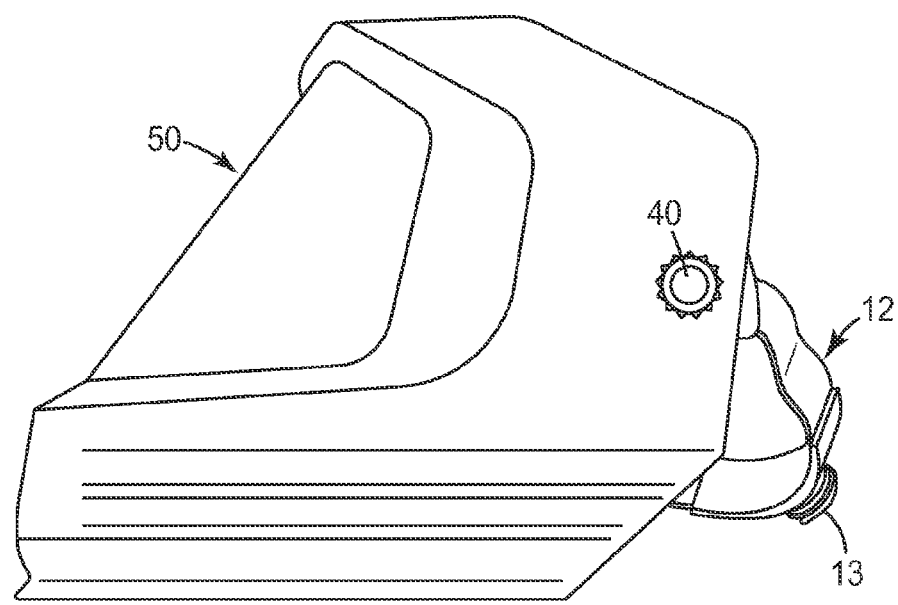
FIG. 3 is a schematic side elevation view of an illustrative head protection element.

FIG. 1 is a schematic front perspective view of an illustrative head suspension 10. FIG. 2 is a schematic front elevation view of the illustrative head suspension 10 shown in FIG. 1. FIG. 3 is a schematic side elevation view of an illustrative head protection element 50. The head suspension 10 includes a headband 20 that extends about a user's head 30. The head suspension 10 includes one or more top bands 15 that extend over the user's head 30 and each end of the top band is joined to the headband 20. The head suspension 10 includes a head protection attachment element 40.

The head protection attachment element 40 couples a head protection element to the head suspension 10. In many embodiments, the head protection attachment element 40 pivotally couples a head protection element 50 to the head suspension 10 allowing the head protection element 50 to pivot relative to the head suspension 10. The head protection element 50 can be any useful head protection element such as, for example, a welding helmet or shield, a hard hat, a fire fighter helmet, a grinding shield, sporting equipment headgear and the like.

The headband 20 is an elongated element having a band length and includes a front portion 11 and a rear portion 12. The rear portion 12 can include an adjustment element 13 (shown in FIG. 3) configured to adjust a head size of the head suspension 10. One exemplary adjustment element 13 is an adjustment knob providing a ratchet-type head size adjustment as described in U.S. Pat. No. 4,942,628, and incorporated by reference herein to the extent is does not conflict with the present disclosure. However, any other types of adjustments that enable a user to tighten and/or loosen the head suspension 10 about a users head are within the scope of the present disclosure.

The front portion 11 is configured to be disposed across a forehead 35 of a user 30. The front portion 11 band length extends along a headband plane $H_P$ (a plane extending into the paper through the top of the head 30 and across a forehead 35 of a wearer). A plurality of suspension elements 25 is disposed along the headband length. The plurality of suspension elements 25 is configured to contact the forehead 35 of a user 30. The illustrated headband 20 front portion 11 includes seven suspension elements 25, however it is understood that the headband 20 front portion 11 can include any useful number of suspension elements 25. In many embodiments, the headband 20 front portion 11 includes, for example, a range from 5 to 15 suspension elements 25, or from 5 to 9 suspension elements.

In many embodiments, the suspension elements 25 are uniformly spaced apart along the headband 20 front portion 11. In other embodiments, the suspension elements 25 are not uniformly spaced apart along the headband 20 front portion 11. In some embodiments, the suspension elements 25 are spaced closer together along the headband 20 front portion 11 near the midpoint of the headband 20 front portion 11 length. In many embodiments, the plurality of suspension elements 25 are spaced apart from one another by a distance of at least 1 millimeter, or a distance of at least 5 millimeters, or a distance of at least 10 millimeters.

FIG. 4 is a schematic front plan view of an illustrative head band 20 front portion 11. The suspension elements 25 are generally uniformly spaced apart from each other and joined with the head band 20 front portion 11. The suspension elements 25 extend away from the headband 20 and their projections onto a plane of a major surface of the headband 20 are, in many embodiments, orthogonal to the elongated headband 20 length.

FIG. 5 is a schematic perspective view of an illustrative suspension element 25. FIG. 6 is a schematic perspective view of an illustrative contact pad 27. The illustrated suspension element 25 includes a forehead contact pad 27 spaced apart from the elongated headband 20 and joined or connected to the headband 20 with a strut element 26.

In many embodiments, the suspension element 25 includes two strut elements 26 forming a strut element pair. In many embodiments, each strut element 26 of the strut element pair is attached to a forehead contact pad 27. In many embodiments, each strut element 26 of the pair is attached or joined to the headband 20 at a location along the elongated headband 20. The strut elements 26 of a pair extend away from each other and away from the elongated headband 20. In some embodiments, the strut element pairs are joined to the elongated headband and at least a portion 21 of the elongated headband 20 is disposed between the opposing strut elements 26. The illustrated embodiment shows corresponding forehead contact pads 27 in registration for each strut element pair, or disposed symmetrically with respect to each other with respect to the headband 20.

In typical embodiments, at least portions of the one or more of the suspension elements 25 do not lie in the same plane as adjacent portions of the headband 20. In many embodiments, the one or more of the strut elements 26 are curved into or toward the forehead 35 of the user 30 (see FIG. 1). In many embodiments, the forehead contact pad 27 has a curved or non-planar forehead contact surface 28. In other embodiments, the forehead contact pad 27 has a planar forehead contact surface 28. In some embodiments, one or more of, or at least selected suspension elements 25, or forehead contact pads 27 are removable, detachable, or replaceable from the headband 20. In other exemplary embodiments, one or more of the suspension elements 25 or at least the strut elements 26 are permanently attached to, e.g., formed integrally with, the elongated headband 20.

The strut elements 26 and/or forehead contact pads 27 can be formed of a resilient material such as, for example, a polymeric material. The resilient material allows each suspension element 25 to flex or conform to the user's unique forehead contours. The forehead contact pads 27 increase the amount of contact surface area, spreading out the force applied to the user's unique forehead and reducing discomfort, as compared to traditional designs. In many embodiments, the amount of local pressure applied by each forehead contact pad 27 (when used in conjunction with a traditional welding helmet) is less than 20 kPa, or less than 15 kPa, or less than 10 kPa. In some embodiments, the forehead contact pads 27 can be formed of a softer and/or an absorbent material or covered with a softer and/or an absorbent material materials such as, for example, a foam material and/or fabric material. These forehead contact pads 27 or portions thereof can be detachable and replaceable, as desired.

Figure 7:
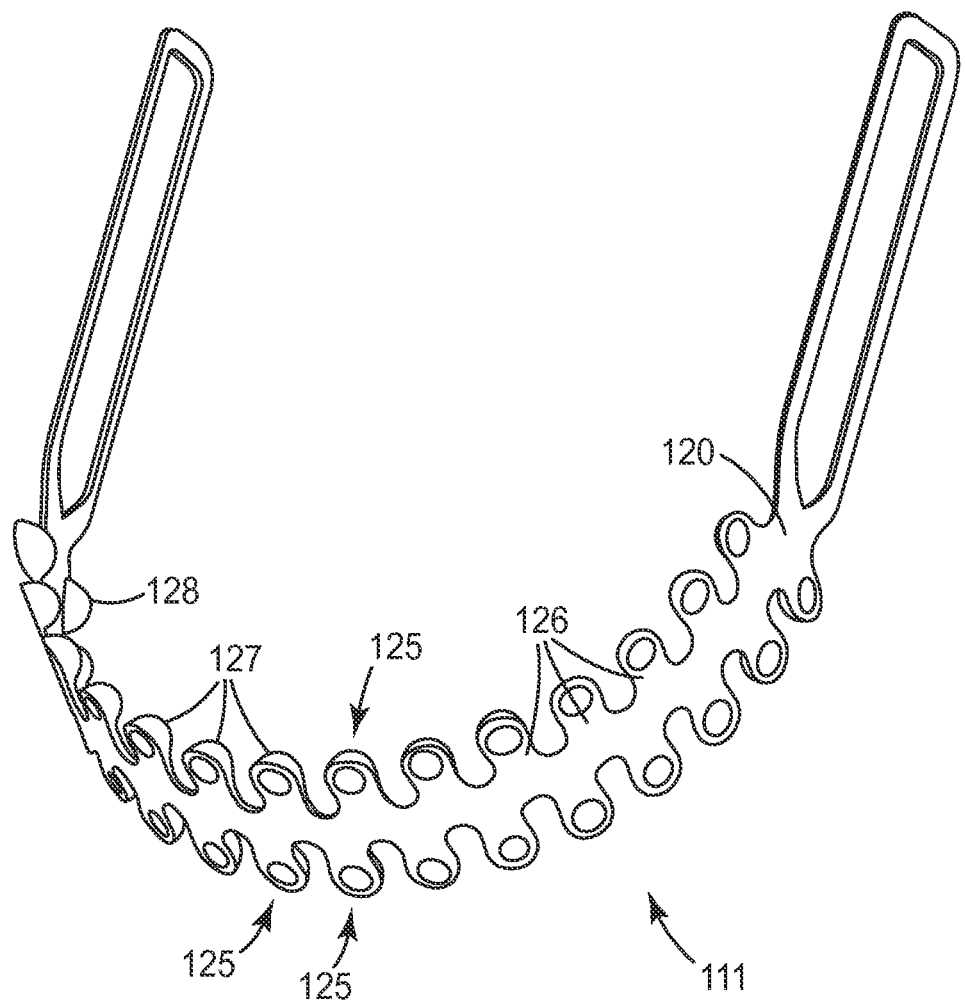
FIG. 7 is a schematic front perspective view of another illustrative head band front portion.

FIG. 7 is a schematic front perspective view of another illustrative head band front portion 111. The front portion 111 is configured to be disposed across a forehead of a user (as shown in FIG. 1 and FIG. 2). The front portion 111 band length extends along a headband plane (as shown in FIG. 2). A plurality of suspension elements 125 is disposed along the headband length. The plurality of suspension elements 125 is configured to contact the forehead of a user. The illustrated headband 120 front portion 111 includes fourteen suspension elements 125, however it is understood that the headband 120 front portion 111 can include any useful number of suspension elements 125. In many embodiments, the headband 120 front portion 111 includes a range from 5 to 25 suspension elements 125, or from 5 to 17 suspension elements.

The suspension elements 125 are generally uniformly spaced apart from each other and joined with the headband 120 front portion 111. The suspension elements 125 extend away from the headband 120 and their projections onto a plane of the major surface of the headband 120 are orthogonal to the elongated headband 120 length. Each illustrated suspension element 125 includes a forehead contact pad 127 spaced apart from the elongated headband 120 and joined or connected to the headband 120 with a strut element 126.

In this exemplary embodiment, at least portions of the one or more of the suspension elements 125 do not lie in the same plane as adjacent portions of the headband 120. In many embodiments, the strut elements 126 are planar elements. In other embodiments, the strut elements 126 can be curved elements that curve into or toward the forehead of the user (see FIG. 1). In the illustrated embodiment, the forehead contact pad 127 has a curved or non-planar forehead contact surface 128. The illustrated forehead contact pads 127 have a hemispherical shape. In some embodiments, one or more of, or at least selected suspension elements 125, or forehead contact pads 127 are removable, detachable, or replaceable from the headband 120. The illustrated embodiment shows corresponding upper and lower forehead contact pads 127 staggered along the length of the headband 120 front portion 111.

The strut elements 126 and/or forehead contact pads 127 can be formed of a resilient material such as, for example, a polymeric material. The resilient material allows each suspension element 125 to flex or conform to the user's unique forehead contours. The forehead contact pads 127 increase the amount of contact surface area, spreading out the force applied to the user's unique forehead and reducing discomfort, as compared to traditional designs. In many embodiments, the amount of local pressure applied by each forehead contact pad 127 (when used in conjunction with a traditional welding helmet) is less than 20 kPa, or less than 15 kPa, or less than 10 kPa.

Thus, embodiments of the HEAD SUSPENSION HEADBAND are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A head suspension headband comprising:
   an elongated headband having a band length and configured to be disposed across a forehead of a user; and
   a plurality of suspension elements disposed along the band length and configured to contact the forehead of a user;
   wherein at least selected suspension elements each comprise a forehead contact pad,
   wherein each selected suspension element and the forehead contact pad thereof is integrally formed with the elongated headband and is joined to an adjacent portion thereof by a strut element,
   wherein each strut element of a selected suspension element is curved inwardly toward the forehead of a user so that the forehead contact pad of the selected suspension element does not lie in the same plane as the adjacent portion of the elongated headband to which it is joined by a strut element,
   and wherein the head suspension headband comprises a head protection attachment element that is configured to pivotably couple a head protection element to the head suspension headband.

2. A head suspension headband according to claim 1, wherein the forehead contact pads are spaced apart from the elongated headband.

3. A head suspension headband according to claim 1, wherein the head protection element is chosen from the group consisting of a welding helmet or shield, a hard hat, and a grinding shield.

4. A head suspension headband according to claim 1, wherein the strut elements form strut element pairs and each strut element pair is attached to a location along the elongated headband and each strut element pair comprises two strut elements that extend away from each other and away from the elongated headband.

5. A head suspension headband according to claim 4, wherein each forehead contact pad in the strut element pair is attached to a single strut element.

6. A head suspension headband according to claim 1, wherein at least selected suspension elements are removable from the elongated headband.

7. A head suspension headband according to claim 2, wherein at least selected strut elements extend away from the elongated headband and their projections onto a plane of a major surface of the headband are orthogonal to the elongated headband length.

8. A head suspension headband according to claim 4, wherein at least selected strut element pairs each comprises two strut elements that are joined to the elongated headband and at least a portion of the elongated headband is disposed between the two strut elements.

9. A head suspension headband according to claim 1, wherein the elongated headband comprises a band length and comprises an adjustment element configured to reversibly adjust a head size of the headband.

10. A head protection device comprising;
    a head suspension headband comprising an elongated headband having a band length and configured to be disposed across a forehead of a user, and a plurality of suspension elements disposed along the band length comprising forehead contact pads configured to contact the forehead of a user,
    wherein the forehead contact pads increase the amount of contact surface area to spread out force from the headband applied to a user's forehead,
    wherein at least a selected suspension element and the forehead contact pad thereof is integrally formed with the elongated headband and is joined to an adjacent portion thereof by a strut element, and
    wherein the strut element of the selected suspension element is curved inwardly toward the forehead of a user so that the forehead contact pad of the selected suspension element does not lie in the same plane as the adjacent portion of the elongated headband to which it is joined by the strut element;
    and a head protection element attached to the head suspension headband.

11. A head protection device according to claim 10, wherein the head protection element is a protective shield.

12. A head protection device according to claim 10, wherein the head protection element is a welding helmet.

13. A head protection device according to claim 10, wherein the forehead contact pads are spaced apart from the elongated headband.

14. A head protection device according to claim 13, wherein each suspension element comprises a pair of strut elements that extend away from each other and away from the elongated headband and a forehead contact pad attached to each strut element.

15. A head protection device according to claim 14, wherein at least selected strut element pairs comprise two strut elements that are joined to the elongated headband and at least a portion of the elongated headband is disposed between the two strut elements.

16. A head protection device according to claim 14, wherein a first forehead contact pad that is attached to a first strut element of the pair of strut elements, comprises a generally U-shaped first main body with an open end of the U facing the adjacent portion of the elongated band to which the first forehead contact pad is connected by the first strut element;

and, wherein a second forehead contact pad that is attached to a second strut element of the pair of strut elements, comprises a generally U-shaped second main body with an open end of the U facing the adjacent portion of the elongated band to which the first and second forehead contact pads are connected by the first and second strut elements.

17. A head protection device according to claim 10, wherein the elongated headband comprises a band length and comprises an adjustment element configured to reversibly adjust a head size of the headband.

18. A head protection device according to claim 10, wherein at least selected suspension elements each comprise a forehead contact pad with a planar forehead contact surface.

19. A head protection device according to claim 10, wherein at least selected suspension elements each comprise a forehead contact pad with a curved forehead contact surface.

* * * * *

UNITED STATES PATENT AND TRADEMARK OFFICE
CERTIFICATE OF CORRECTION

| | |
|---|---|
| PATENT NO. | : 8,453,268 B2 |
| APPLICATION NO. | : 12/681847 |
| DATED | : June 4, 2013 |
| INVENTOR(S) | : Lars-Olov Ahlgren et al. |

It is certified that error appears in the above-identified patent and that said Letters Patent is hereby corrected as shown below:

In the Claims

Column 6
Line 39, In Claim 8, delete "comprises" and insert -- comprise --, therefor.

Signed and Sealed this
Eleventh Day of February, 2014

Michelle K. Lee
*Deputy Director of the United States Patent and Trademark Office*